United States Patent
Burnet et al.

(10) Patent No.: US 7,271,154 B2
(45) Date of Patent: Sep. 18, 2007

(54) ANTIBIOTIC CONJUGATES

(75) Inventors: Michael Burnet, Kusterdingen (DE); Jan-Hinrich Guse, Tubingen-Buhl (DE); Gene Kim, Tubingen (DE)

(73) Assignee: Merckle GmbH, Munich (DE)

( * ) Notice: Subject to any disclaimer, the term of this patent is extended or adjusted under 35 U.S.C. 154(b) by 55 days.

(21) Appl. No.: 10/367,104

(22) Filed: Feb. 14, 2003

(65) Prior Publication Data

US 2004/0033969 A1 Feb. 19, 2004

Related U.S. Application Data

(60) Provisional application No. 60/357,584, filed on Feb. 15, 2002.

(51) Int. Cl.
C07H 17/08 (2006.01)
A61K 31/335 (2006.01)

(52) U.S. Cl. .................. 514/29; 514/183; 540/450; 540/467; 540/480

(58) Field of Classification Search ............. 540/467, 540/480, 450; 514/29, 183
See application file for complete search history.

(56) References Cited

U.S. PATENT DOCUMENTS

| | | | | |
|---|---|---|---|---|
| 3,417,077 | A | 12/1968 | Murphy et al. | 260/210 |
| 3,884,903 | A | 5/1975 | Jones et al. | 260/210 |
| 4,328,334 | A | 5/1982 | Kobrehel et al. | 536/7.4 |
| 4,382,086 | A | 5/1983 | Sciavolino et al. | 424/180 |
| 4,474,768 | A | 10/1984 | Bright | 424/180 |
| 4,517,359 | A | 5/1985 | Kobrehel et al. | 536/7.4 |
| 4,834,973 | A | 5/1989 | Strahilevitz | 424/175.1 |
| 5,466,681 | A | 11/1995 | Krivan et al. | |
| 5,486,536 | A | 1/1996 | Ward et al. | |
| 5,516,864 | A | 5/1996 | Kuhn et al. | 526/263 |
| 5,676,971 | A | 10/1997 | Yoshioka et al. | 424/450 |
| 5,750,493 | A | 5/1998 | Sommadossi et al. | 514/1 |
| 5,827,533 | A | 10/1998 | Needham | 424/450 |
| 5,846,458 | A | 12/1998 | Yoshioka et al. | 264/4.32 |
| 5,928,868 | A | 7/1999 | Liu et al. | |
| 6,043,227 | A | 3/2000 | Cheng et al. | 514/29 |
| 6,300,316 | B1 | 10/2001 | Brighty et al. | 514/29 |
| 6,562,796 | B2 | 5/2003 | Baldwin et al. | 514/31 |
| 2003/0068362 | A1 | 4/2003 | Soon-Shiong et al. | |

FOREIGN PATENT DOCUMENTS

| | | |
|---|---|---|
| EP | 0009944 B1 | 4/1980 |
| EP | 0044090 | 1/1982 |
| EP | 0159856 | 10/1985 |
| EP | 0189281 | 7/1986 |
| EP | 0895999 A1 * | 7/1988 |
| EP | 0467331 B1 | 1/1992 |
| EP | 0895999 A1 | 2/1999 |
| EP | 0984019 A1 | 3/2000 |
| EP | 0992509 A2 | 4/2000 |
| EP | 1088828 A2 | 4/2001 |
| EP | 1122261 A2 | 8/2001 |
| EP | 1167376 A1 | 1/2002 |
| EP | 1 036 083 B1 | 5/2004 |
| JP | 05163293 A | 6/1993 |
| WO | WO99/51616 | 10/1999 |
| WO | WO-99/63937 | 12/1999 |
| WO | WO-99/64032 | 12/1999 |
| WO | WO-99/64040 | 12/1999 |
| WO | WO-02/055531 A1 | 7/2002 |
| WO | WO 03/045319 * | 6/2003 |

OTHER PUBLICATIONS

International Search Report for PCT/US03/04596.
Ianaro et al., "Anti-Inflammatory Activity of Macrolide Antibiotics", Jan. 2000, J. Pharmacology and Experimental Therapeutics, vol. 292, No. 1, pp. 156-163.
N. Shibata, et al., "Relationship between erythrocyte-to-plasma distribution ratio of cyclosporin and lymphocyte proliferation in renal transplant patients," Eur. J. Clin. Pharmacol., vol. 51, pp. 455-459 (1997).
Goodman and Giman's: The Pharmacalogical Basis of Therapeutics, 10th Edition, McGraw Hill Medical Publishing Division, pp. 54-57 (2001).

* cited by examiner

*Primary Examiner*—Zinna N. Davis
(74) *Attorney, Agent, or Firm*—Edwards Angell Palmer & Dodge LLP; Jeffrey D. Hsi

(57) ABSTRACT

This invention features a compound of the following formula:

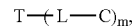

$$T-(L-C)_m,$$

wherein T is a transportophore, L is a bond or linker, and C is an antibiotic therapeutic agent, the transportophore is covalently bonded to the antibiotic therapeutic agent via the bond or the linker, and the transportophore is an azithromycin derivative or crown ether derivative.

10 Claims, No Drawings

ANTIBIOTIC CONJUGATES

CROSS-REFERENCE TO RELATED APPLICATIONS

This application claims benefit of U.S. provisional application No. 60/357,584, filed Feb. 15, 2002, the contents of which are incorporated herein by reference.

BACKGROUND

Phagocytic white blood cells and antimicrobial agents have been recognized as having several potential interactions that may be synergistic for combating infection. Phagocytic killing by polymorphonuclear leukocytes (PMNs), monocytes, and macrophages is the primary host defense against bacterial infections. Antimicrobial agents make bacteria more susceptible to killing by neutrophils even at subinhibitory concentrations (Adinolfi & Bonventre (1988) *Antimicrob Agents Chemother* 32: 1012-8). Neutrophils migrate to sites of infection, concentrate at these sites, and thus may serve as an antimicrobial agent delivery mechanism.

Despite the effectiveness of this defense, *Salmonella* and other intracellular pathogens can invade phagocytes and survive inside them, avoiding the lysosomal compartment. Cellular invasion is an important step in the progression of many serious bacterial infections because it allows pathogens to evade host defense mechanisms and benefit from a rich nutrient supply.

In order for neutrophils to function as an effective means of transporting antimicrobial agents to sites of infection, several criteria must be met: the agent should not interfere with neutrophil migration, the agent should be concentrated in the neutrophil, and the agent should be released in an active form at the site of infection.

Cell-permeating antimicrobial agents can potentially play an important role in eliminating infections by intracellular pathogens. Unfortunately, many antibiotic classes do not penetrate the plasma membrane effectively (See, for example, Table 1). β-lactam and cephalosporins, while representing one of the most prescribed antibiotics today, suffer from poor intracellular penetration and therefore have limited utility in the treatment of intracellular bacterial pathogens. Therefore, the effectiveness of an antimicrobial agent in vivo depends not only on its activity but also on its ability to reach sites of infection.

TABLE 1

Antimicrobial agent uptake by PMN[a]

| Agent | Concn (mg/ml) | | I/E ratio |
|---|---|---|---|
| | Extracellular | Intracellular | |
| Azithromycin | 0.1 | 51.7 ± 4.3 | 517 |
| Ciprofloxacin | 4.0 | 24.8 ± 4.8 | 6.2 |
| Levofloxacin | 6.0 | 28.8 ± 4.8 | 4.8 |
| Moxifloxacin | 4.5 | 54 ± 10.5 | 12.0 |
| Penicillin G | 10 | 1.6 ± 0.2 | 0.16 |
| Telithromycin | 0.1 | 19.7 ± 2.7 | 197 |

[a]Extracellular and intracellular antimicrobial agent concentrations for PMN incubated with the indicated concentrations of antimicrobial agents for 1 h were determined by bioassay. Results are means of at least three determinations.

One class of antibiotics which have shown promise both in terms of accumulation in phagocytic white blood cells as well as in fighting intracellular infections has been macrolides. Certain members of the macrolide antibiotic family accumulate to a large degree in phagocytic cells, often achieving a cellular-to-extracellular concentration ratio (C/E) of greater than 100. In particular, Azithromycin, an azalide antibiotic (see, e.g., Djokic et al. (1988) *J. Chem. Res.* 152: 1239-61; Bright et al. (1988) *J. Antibiot.* 41: 1029-47; and U.S. Pat. No. 4,474,768) is more stable than erythromycin in the presence of acids, and has very low plasma concentrations owing to its concentration to a large extent in cells, often achieving a C/E of ~500 (Bouvier d'Yvoire et al. (1998) *J. Antimicrob. Chemother.* 41: Suppl. B, 63-68). Its stability, accumulation in phagocytes and long half-life ($t_{1/2}$~68 hours), make azithromycin an ideal antibiotic in terms of in vivo distribution.

In spite of the ideal intracellular distribution of macrolide antibiotics, resistance is emerging among bacterial pathogens (see, e.g., Singh et al. (2001) *Antimicrob Agents Chemother* 45: 263-266; Occhialini et al. (1997) *Antimicrob Agents Chemother* 47: 2724-2728; and Nash (2001) *Antimicrob. Agents Chemother.* 45: 1607-1614). It is clear that development of more intracellularly accumulating antibiotics, whether new or existing, will greatly enhance treatment of various infectious diseases.

In general, successful therapy with a pharmaceutical agent requires that the agent satisfy numerous requirements imposed by the physiology of the host and of the disease or condition. These include: (i) adequate ability to interact with the target; (ii) appropriate physical properties for presence at the location of the receptors in concentrations that permit the interactions noted above; (iii) appropriate physical properties to allow the agent to enter the body and distribute to the location of the receptors by any means; (iv) Sufficient stability in fluids of the body; (v) the absence of toxic effects in compartments where the drug is most concentrated, or in any other compartment where the drug is located; and (vi) the absence of sequestration into non-physiological compartments and so on.

In general, these compounding requirements limit the nature of pharmaceutical compounds that have utility in vivo and thus reduce the probability of discovering adequately active molecules from de novo starting points.

Current strategies for enhancing the intracellular accumulation of antibiotics include direct chemical modification of regions within the antibiotic, incorporation of antibiotics into liposomes, or the preparation of prodrugs. Recent improvements in the technology of synthetic chemistry and molecular biology have allowed the testing of large numbers of structural variants and the discovery of many ligands with adequate affinity to their targets to have some potential in vivo. Many such molecules prove inadequate on in vivo testing largely due to the manifold, stringent, and often conflicting (i.e., stability without toxicity) requirements outlined above.

U.S. Pat. No. 5,434,147 describes a process for conjugation of antibiotics with transferrin or low density lipoprotein for treating intracellular pathogens. The coupled transferrin molecules are claimed to be selectively taken up by phagosomes to target membrane-bound pathogens. However, transferrin, and therefore molecules attached to it, do not traffic through the lysosomal compartment. This process, therefore, is of limited utility in areas where the antibiotic is to provide synergistic activity with phagocytic immune cells in neutralising non-intracellular pathogens. Furthermore, the molecular weight of transferrin (76,000-81,000 daltons), as well as its polypeptide composition, precludes oral delivery of such compositions. Oral absorption of drugs is the most desirable method of drug administration in the treatment of human diseases, particularly in prolonged therapeutical treatments.

One class of antibiotics which have shown promise both in terms of accumulation in phagocytic white blood cells as well as in fighting intracellular infections has been macrolides. Certain members of the macrolide antibiotic family accumulate to a large degree in phagocytic cells, often achieving a cellular-to-extracellular concentration ratio (C/E) of greater than 100. In particular, Azithromycin, an azalide antibiotic (Djokic et al., supra; Bright et al., supra; and U.S. Pat. No. 4,474,768) is more stable than erythromycin in the presence of acids, and has very low plasma concentrations owing to its concentration to a large extent in cells, often achieving a C/E of ~500 (Bouvier d'Yvoire et al., supra). Its stability, accumulation in phagocytes and long half-life (t½~68 hours), make azithromycin an ideal antibiotic in terms of in vivo distribution.

SUMMARY

The invention relates to a conjugate useful for enhancing efficacy of a therapeutic agent, and a method of treating diseases including infection diseases (e.g., bacterial diseases).

In one aspect, this invention features a compound of the following formula:

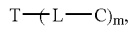

wherein T is a transportophore, L is a bond or linker, C is an antibiotic therapeutic agent, and m is 1-8, the transportophore is covalently bonded to the antibiotic therapeutic agent via the bond or the linker, and the transportophore is an azithromycin derivative or crown ether derivative. Note that when there are more than one L or C moieties (i.e., m is greater than 1), the L moieties or the C moieties, independently, can be the same or different.

The transportophore can be a metabolite, a natural product, a metabolite mimic, a metabolite derivative (e.g., a sugar, amino, or peptide derivative), a fatty acid, a bile acid, a vitamin, a nucleobase, an alcohol, or an organic acid or base, a portion of which resembles and is recognized as a substrate for transport protein(s). It can be an amphiphilic molecule having a pKa value of 6.5 to 9.5, or a cyclic or heterocyclic molecule (e.g., lactone, lactam, ether, cyclic acetal or hemi-acetal). The cyclic or heterocyclic molecule can have an attached sugar. The cyclic or heterocyclic molecule can be a macrolactone or macroether, including a macrolactone or macroether having an attached sugar. The cyclic or heterocyclic molecule can also be a macrolide or ketolide having an amino sugar, including a macrolide having mono-, di-, or tri-basic groups (e.g., an amine). In some embodiments, the macrolide has no intrinsic antibacterial activity (determined by, e.g., an antibiotic sensitivity test) at 10 µM in solution and a pKa value between 6.5 and 9.0

In some embodiments, the transportophore is an azithromycin derivative, and the conjugate has the formula (in which a bond, drawn without any attached groups, means a methyl group. The same rule applies to other similar situations):

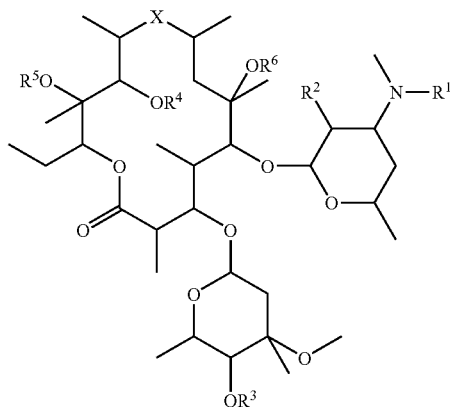

wherein
X=N($R_7$)—$CH_2$
$CH_2$—N($R_7$)
C(=O)
C(=NO$R_8$)
C(OH)($R_9$)
CH(N$R_{10}R_{11}$)
C(=N$R_{12}$)
Y=independently, a bond or a linker (alkylating residue or neighbouring a carbonyl)
Z=C(=O)
CH($R_{16}$)
$R_1$=H
$CH_3$
($C_2$-$C_{10}$)alkyl
($C_1$-$C_{10}$)alkenyl
($C_1$-$C_{10}$)alkynyl
($C_1$-$C_8$)[($C_1$-$C_4$)alkoxy]alkyl
($C_1$-$C_8$)[($C_1$-$C_4$)alkoxy]alkenyl
($C_6$-$C_{10}$)aryl-($C_1$-$C_5$)alkyl
($C_2$-$C_9$)heteroaryl-($C_1$-$C_5$)alkyl
($C_1$-$C_4$)alkyliden-N$R_{18}R_{19}$
Y—$R_{13}$
C(=O)—Y—$R_{15}$
C(=O)—$R_{15}$
$R_2$=H
OH
S$CH_3$;
$R_3$=H
C(=O)—Y—$R_{15}$
C(=O)—$R_{15}$
$R_4$=H
C(=O)—Y—$R_{15}$
C(=O)—$R_{15}$
$R_5$=H
or $R_4$ and $R_5$ are connected by Z;
$R_6$=H
$CH_3$
$R_7$=H
$CH_3$
Y—$R_{13}$
C(=O)—Y—$R_{15}$
C(=O)—$R_{15}$
$R_8$=H
Y—$R_{13}$
C(=O)—$R_{17}$
$R_9$=H
($C_1$-$C_{10}$)alkyl ($C_1$-$C_{10}$)alkenyl
($C_1$-$C_{10}$)alkynyl
($C_1$-$C_8$)[($C_1$-$C_4$)alkoxy]alkyl
($C_1$-$C_8$)[($C_1$-$C_4$)alkoxy]alkenyl
($C_6$-$C_{10}$)aryl-($C_1$-$C_5$)alkyl
($C_2$-$C_9$)heteroaryl-($C_1$-$C_5$)alkyl $R_{10}$, $R_{11}$=independently, H
($C_1$-$C_{10}$)alkyl
($C_1$-$C_{10}$)alkenyl
($C_1$-$C_{10}$)alkynyl
($C_1$-$C_8$)[($C_1$-$C_4$)alkoxy]alkyl
($C_1$-$C_8$)[($C_1$-$C_4$)alkoxy]alkenyl
($C_6$-$C_{10}$)aryl-($C_1$-$C_5$)alkyl
($C_2$-$C_9$)heteroaryl-($C_1$-$C_5$)alkyl
($C_1$-$C_4$)alkyliden-$NR_{18}R_{19}$
or $R_{10}$=H and $R_{11}$=Y—$R_{13}$
C(=O)—Y—$R_{15}$
C(=O)—$R_{15}$ $R_{12}$=independently, H
($C_1$-$C_{10}$)alkyl
($C_1$-$C_{10}$)alkenyl
($C_1$-$C_{10}$)alkynyl
($C_1$-$C_8$)[($C_1$-$C_4$)alkoxy]alkyl
($C_1$-$C_8$)[($C_1$-$C_4$)alkoxy]alkenyl
($C_6$-$C_{10}$)aryl-($C_1$-$C_5$)alkyl
($C_2$-$C_9$)heteroaryl-($C_1$-$C_5$)alkyl
($C_1$-$C_4$)alkyliden-$NR_{18}R_{19}$
Y—$R_{13}$ $R_{13}$=independently, an antibiotic therapeutic agent
$R_{15}$=independently, an antibiotic therapeutic agent
$R_{16}$=independently, H
$CH_3$
($C_2$-$C_{10}$)alkyl
($C_1$-$C_{10}$)alkenyl
($C_1$-$C_{10}$)alkynyl
($C_1$-$C_8$)[($C_1$-$C_4$)alkoxy]alkyl
($C_1$-$C_8$)[($C_1$-$C_4$)alkoxy]alkenyl
($C_6$-$C_{10}$)aryl-($C_1$-$C_5$)alkyl
($C_2$-$C_9$)heteroaryl-($C_1$-$C_5$)alkyl
($C_1$-$C_4$)alkyliden-$NR_{18}R_{19}$
Y—$R_{13}$, $R_{17}$=(O—$R_{20}$-aryliden)($C_1$-$C_{10}$)alkyl
$R_{18}$, $R_{19}$=independenly, H
($C_1$-$C_{10}$)alkyl
($C_1$-$C_{10}$)alkenyl
($C_1$-$C_{10}$)alkynyl
($C_1$-$C_8$)[($C_1$-$C_4$)alkoxy]alkyl
($C_1$-$C_8$)[($C_1$-$C_4$)alkoxy]alkenyl
($C_6$-$C_{10}$)aryl-($C_1$-$C_5$)alkyl
($C_2$-$C_9$)heteroaryl-($C_1$-$C_5$)alkyl $R_{20}$=independently, Halogen
($C_1$-$C_3$)alkyl
$NO_2$
CN
$OCH_3$
$N(CH_3)_2$.

In some other embodiments, the transportophore is a crown ether derivative, and the conjugate has the formula:

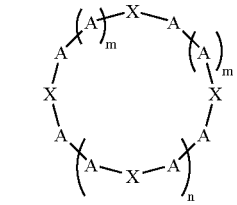

wherein
m=independently, 0, 1, 2, or 3
n=0-7
X=independently, O
S
Se
$NR^1$
$PR^1$
in which at least one of X is $NR^1$;
A=independently, $CH_2$
$CHR^2$
$CR^2R^3$
C(=O)
in which at least one of (A-X) is not an amide;
$R^1$=independently, H
($C_1$-$C_{10}$)alkyl, optionally substituted with fluoro, cyano, $R^4$, $R^4O_2C$,
$R^4C$(=O)NH, and $R^4S$(=O)$_k$ wherein k is 0, 1 or 2
$R^4C$(=O), $R^4S$(=O)$_k$ wherein k is 0, 1 or 2
$R_2$, $R^3$=independently, $NH_2$
$NHR^1$
$NR^1R^5$
OH,
$OR^4$
$R^4C$(=O) ($C_1$-$C_6$)alkyl
($C_2$-$C_{12}$)alkenyl
($C_2$-$C_{12}$)alkynyl
($C_3$-$C_{10}$)cycloalkyl($C_1$-$C_6$)alkyl
($C_2$-$C_9$)heterocycloalkyl($C_1$-$C_6$)alkyl
($C_6$-$C_{10}$)aryl($C_1$-$C_6$)alkyl
($C_2$-$C_9$)heteroaryl($C_1$-$C_6$)alkyl,
in which the alkyl, alkenyl, alkynyl, cycloalkyl, heterocycloalkyl, aryl, or heteroaryl is optionally substituted, independently, with 1-3 halogens, ($C_1$-$C_4$)alkoxy, hydroxy, nitro, cyano, —C(=O)—$OR^8$, —C(=O)N(H)$R^8$, ($C_6$-$C_{10}$)aryl, ($C_2$-$C_9$)heteroaryl, $NR^5R^6R^7$, or an antibiotic therapeutic agent;
$R^4$=independently, $NH_2$
$NHR^9$
$NR^9R^5$
OH
$OR^9$
($C_1$-$C_6$)alkyl
($C_2$-$C_{12}$)alkenyl
($C_2$-$C_{12}$)alkynyl
($C_3$-$C_{10}$)cycloalkyl($C_1$-$C_6$)alkyl
($C_2$-$C_9$)heterocycloalkyl($C_1$-$C_6$)alkyl
($C_6$-$C_{10}$)aryl($C_1$-$C_6$)alkyl
($C_2$-$C_9$)heteroaryl($C_1$-$C_6$)alkyl,
in which the alkyl, alkenyl, alkynyl, cycloalkyl, heterocycloalkyl, aryl, or heteroaryl is optionally substituted, independently, with 1-3 halogens, ($C_1$-$C_4$)alkoxy, hydroxy, nitro, cyano, —C(=O)—$OR^8$, —C(=O)N(H)$R^8$, ($C_6$-$C_{10}$)aryl, ($C_2$-$C_9$)heteroaryl, $NR^5R^6R^7$, or an antibiotic therapeutic agent;

$R^5$, $R^6$=independently, H
    ($C_1$-$C_6$), optionally substituted by hydroxy
    ($C_6$-$C_{10}$)aryl
    ($C_2$-$C_9$)heteroaryl
$R^7$=independently, lone electron pair
    $CH_3$
    $C_2H_5$
    $C_3H_7$
    $CH_2$-$C_6H_5$
$R^8$=independently, an antibiotic therapeutic agent
$R^9$=independently, ($C_1$-$C_6$) alkyl
    ($C_2$-$C_{12}$)alkenyl
    ($C_2$-$C_{12}$)alkynyl
    ($C_3$-$C_{10}$)cycloalkyl($C_1$-$C_6$)alkyl
    ($C_2$-$C_9$)heterocycloalkyl($C_1$-$C_6$)alkyl
    ($C_6$-$C_{10}$)aryl($C_1$-$C_6$)alkyl or
    ($C_2$-$C_{10}$)heteroaryl($C_1$-$C_6$)alkyl, in which the alkyl, alkenyl, alkynyl, cycloalkyl, heterocycloalkyl, aryl, or heteroaryl is optionally substituted, independently, with 1-3 halogens, ($C_1$-$C_4$)alkoxy, hydroxy, nitro, cyano, —C(=O)—$OR^8$, —C(=O)N(H)$R^8$, ($C_6$-$C_{10}$)aryl, ($C_2$-$C_{10}$)heteroaryl, $NR^5R^6R^7$, or an antibiotic therapeutic agent.

The transportophore is covalently bonded to an antibiotic therapeutic agent. The linker can be ($C_1$-$C_8$)alkyl, ($C_1$-$C_8$)alkenyl, ($C_1$-$C_8$)alkynyl, ($C_3$-$C_{10}$)cycloalkyl, ($C_6$-$C^{10}$)aryl, ($C_2$-$C_9$)heteroalkyl, or ($C_2$-$C_9$)heteroaryl; wherein alkyl, alkenyl, alkynyl, cycloalkyl, aryl or heteroaryl is optionally substituted by ($C_1$-$C_6$)alkyl, 1-4 halogens, ($C_1$-$C_4$)alkoxy, ($C_1$-$C_4$)alkoxycarbonyl, hydroxy, amino, ($C_1$-$C_4$)alkylamino, ($C_1$-$C_4$)dialkylamino, ($C_3$-$C_{10}$)cycloalkyl, ($C_1$-$C_6$)alkylcarbonyloxy, ($C_1$-$C_6$)alkylcarbonylamido, ($C_1$-$C_4$)alkylamidocarbonyl, ($C_1$-$C_4$)dialkylamidocarbonyl, nitro, cyano, ($C_1$-$C_4$)alkylimino, mercapto, or ($C_1$-$C_4$)alkylmercapto.

In some embodiments, the linker can be added in one or more positions via one or more linking groups of the same or differing formula. In a single embodiment providing for more than one position to be occupied by any molecule defined as above, there is no requirement for all linkers to be the same molecule. Indeed, in some embodiments, it will be desirable that more than one linker is linked to a transportophore and that the linkers be two different molecules as is exemplified in the examples (see, e.g., Example 1, Synthesis 2). The linker can be many other molecules that, to date, have not been classified as pharmacological agents and commercialised as such due to inadequate pharmacokinetic properties including one or more of those listed below. Given the data presented herein, it would be desirable to attach a novel agent potentially active in the indication areas cited herein to a linker in an attempt to capture the in vivo benefits that the linker may confer.

A "therapeutic agent," as used herein, is a molecule with pharmacological activity (e.g., a drug, medicine, medicament, or active agent), a disease modification agent, or any other molecule that can be covalently attached to a transportophore via a bond or a linker which may have a desirable mode of action in bacterial cells. A therapeutic agent may be released from a compound described above in response to the enzyme activity or the physicochemical environment of the targeted cells. Thus, the therapeutic agent is selectively accumulated in a cell due to specific characteristics of the cell membranes, specific expression of membrane proteins, specific conditions within the cell, notably to expression of specific proteins such as granule proteins, binding sites in the cytoplasm, or other membrane bound or soluble proteins, and is thus trapped in the cell and therefore exhibits an enhanced or desired activity therein. An "amphiphilic molecule," as used herein, is a molecule having a hydrophilic (polar) and hydrophobic (non-polar) functional groups (e.g., atoms) or a combination of groups (or atoms). The pKa of this molecule is in the range of 6.5 to 9.5.

The term "sugar" refers to a mono-, di-, or tri-saccharide including deoxy-, thio-, and amino-saccharides. Examples of sugar include, but are not limited to, furanose and pyranose.

The term "macrolactone" refers to a large lactone ring (i.e., cyclic ester) having at least 10 (e.g., 10 to 25) ring atoms.

The term "macrocyclic ether" refers to an ether having at least 10 (e.g., 10 to 25) ring atoms.

The term "macrolide" refers to a chemical compound characterized by a large lactone ring (having at least 10, e.g., 10 to 25, ring atoms) containing one or more keto and hydroxyl groups, or to any of a large group of antibacterial antibiotics containing a large lactone ring linked glycosidically to one or more sugars; they are produced by certain species of *Streptomyces* and inhibit protein synthesis by binding to the 50S subunits of 70S ribosomes. Examples include *erythromycin, azithromycin*, and *clarithromycin*.

The term "ketolide" refers to a chemical compound characterized by a large lactone ring (having at least 10, e.g., 10 to 25, ring atoms) containing one or more keto groups.

The term "phagocytic cell" refers to a cell, especially a leukocyte, that ingests and destroys other cells, microorganisms, or other foreign matter in the blood and tissues.

As used herein, "heteroatom" is a nitrogen, sulfur or oxygen atom. Groups containing one or more heteroatoms may contain different heteroatoms.

"Alkyl" is an unsubstituted or substituted saturated hydrocarbon chain radical having from 1 to 8 carbon atoms, preferably from 1 to 4 carbon atoms. Preferred alkyl groups include (for example) methyl, ethyl, propyl, isopropyl, and butyl.

"Heteroalkyl" is an unsubstituted or substituted saturated chain radical having from 3 to 8 members comprising carbon atoms and one or two heteroatoms.

"Alkenyl" is an unsubstituted or substituted hydrocarbon chain radical having from 2 to 8 carbon atoms, preferably from 2 to 4 carbon atoms, and having at least one olefinic double bond. alkynyl groups have one or more triple carbon-carbon bonds in the chain.

"Cycloalkyl" is a saturated carbocyclic ring radical. Preferred cycloalkyl groups include (for example) cyclopropyl, cyclobutyl and cyclohexyl.

"Heterocyclic ring" is an unsubstituted or substituted, saturated, unsaturated or aromatic ring radical comprised of carbon atoms and one or more heteroatoms in the ring. Heterocyclic rings are monocyclic or are fused, bridged or spiro polycyclic ring systems. Monocyclic rings contain from 3 to 9 atoms, preferably 3 to 6 atoms. Polycyclic rings contain from 7 to 17 atoms, preferably from 7 to 13 atoms.

"Aryl" is an aromatic carbocyclic ring radical. Preferred aryl groups include (for example) phenyl, tolyl, xylyl, cumenyl and naphthyl.

"Heteroaryl" is an aromatic heterocyclic ring radical. Preferred heteroaryl groups include (for example) thienyl, furyl, pyrrolyl, pyridinyl, pyrazinyl, thiazolyl, pyrimidinyl, quinolonyl, and tetrazolyl.

"Alkoxy" is an oxygen radical having a hydrocarbon chain substituent, where the hydrocarbon chain is an alkyl or alkenyl (i.e., —O—alkyl or —O—alkenyl). Preferred alkoxy groups include (for example) methoxy, ethoxy, propoxy and allyloxy.

"Alkylamino" is an amino radical having one or two alkyl substituents (i.e., —N—alkyl).

"Arylalkyl" is an alkyl radical substituted with an aryl group. Preferred arylalkyl groups include benzyl and phenylethyl.

"Arylamino" is an amine radical substituted with an aryl group (i.e., —NH—aryl).

"Aryloxy" is an oxygen radical having a aryl substituent (i.e., —O—aryl).

"Acyl" or "carbonyl" is a radical formed by removal of the hydroxy from an carboxylic acid (i.e., R—C(=O)—). Preferred alkylacyl groups include (for example) acetyl, and propionyl.

"Acyloxy" is an oxygen radical having an acyl substituent (i.e., —O—acyl); for example, —O—C(=O)—alkyl.

"Acylamino" is an amino radical having an acyl substituent (i.e., —N—acyl); for example, —NH—C(=O)—alkyl.

"Alkyliden" is a bivalent alkyl group.

"Aryliden" is a bivalent aryl group.

"Halo", "halogen", or "halide" is a chloro, bromo, fluoro or iodo atom radical. Chloro and fluoro are preferred halides.

Also, as referred to herein, a "lower" hydrocarbon moiety (e.g., "lower" alkyl) is a hydrocarbon chain comprised of from 1 to 6, preferably from 1 to 4, carbon atoms.

Also, as used in defining the structure of the compounds of this invention, a particular radical may be defined for use as a substituent in multiple locations. For example, the $R_{10}a$ substituent is defined as a potential substituent of $R_1$, but is also incorporated into the definition of other substituents (such as $R_3$, $R_8$, and $R_9$). As used herein, such a radical is independently selected each time it is used (e.g., $R_{10a}$ need not be alkyl in all occurrences in defining a given compound of this invention).

The antibiotic therapeutic agent includes an anti-infectious agent (e.g., anti-bacterial).

The compounds described above include the compounds themselves, as well as their salts, if applicable. Such salts, for example, can be formed between a positively charged substituent (e.g., amino) on a compound and an anion. Suitable anions include, but are not limited to, chloride, bromide, iodide, sulfate, nitrate, phosphate, citrate, methanesulfonate, trifluoroacetate, and acetate. Likewise, a negatively charged substituent (e.g., carboxylate) on a compound can form a salt with a cation. Suitable cations include, but are not limited to, sodium ion, potassium ion, magnesium ion, calcium ion, and an ammonium cation such as tetramethylammonium ion.

In addition, some of the compounds of this invention have one or more double bonds, or one or more asymmetric centers. Such compounds can occur as racemates, racemic mixtures, single enantiomers, individual diastereomers, diastereomeric mixtures, and cis- or trans- or E- or Z-double isomeric forms.

Further, the aforementioned compounds also include their N-oxides. The term "N-oxides" refers to one or more nitrogen atoms, when present in a compound, are in N-oxide form, i.e., N→O.

Combinations of substituents and variables envisioned by this invention are only those that result in the formation of stable compounds. The term "stable", as used herein, refers to compounds which possess stability sufficient to allow manufacture and which maintains the integrity of the compound for a sufficient period of time to be useful for the purposes detailed herein (e.g., treating a disease).

In another aspect, this invention features a method for treating an infectious disease (e.g., bacterial disease). The method includes administering to a subject (e.g., mammal, human, dog, cat, horse, cow, chicken, or pig) in need thereof an effective amount of a just described compound, wherein the compound contains an antibiotic therapeutic agent that is an anti-infectious agent. Optionally, the method includes co-usage with other anti-infectious agents or therapeutic agents.

The present invention also features a pharmaceutical composition including at least one compound of this invention and a pharmaceutically acceptable carrier. Optionally, the pharmaceutical composition includes one or more other therapeutic agents.

This invention further features a method for making any of the compounds described above. The method includes taking any intermediate compound delineated herein, reacting it with any one or more reagents to form a compound of this invention including any processes specifically delineated herein.

Also within the scope of this invention is a method for delivering an antibiotic therapeutic agent. The method includes delivering a conjugate described above to a cell (e.g., a phagocytic cell). The conjugate contains a transportophore and an antibiotic therapeutic agent, and in the cell, the transportophore is not covalently bonded to the therapeutic agent.

This invention provides several advantages. For example, the present invention is a widely applicable, pharmacologically viable, method for making prodrugs and the products of this process which will allow the intracellular accumulation of antibiotic compounds. The invention involves the use of azithromycin-derived and crown ether-derived molecules as carriers to provide enhanced intracellular accumulation of antibiotics into phagocytic cells among other cell types. These carriers have been shown to exhibit remarkable accumulation in cells, especially in phagocytic cells. The present invention represents a significant advancement over conventional administration of antibiotics, as it permits the treatment of intracellular pathogens with a wider array of antibiotics than is currently feasible, and, when accumulated within certain cell types, it will have a synergistic effect with the phagocytic killing by polymorphonuclear leukocytes (PMNs), monocytes, and macrophages. Antibiotics previously identified through high-throughput screens which are not in use because of sub-optimal pharmacokinetic behaviour may serve as a suitable drug in this invention, as the pharmacokinetic properties of the carrier is expected to supersede that of the drug.

The broadened range of antibiotics which can be intracellularly accumulated using this invention facilitates the management of troublesome infections caused by pathogens resistant to a restricted set of antibiotics. Intracellular accumulation in the order of C/E~100 also means that intracellular pathogens will receive a correspondingly higher dose of the antibiotic.

Other advantages, objects, and features of the invention will be apparent from the description and from the claims.

DETAILED DESCRIPTION

The present invention relates novel conjugates of antibiotics to carriers consisting of azithromycin-derived or crown ether-derived compounds, as well as methods for synthesising such derivatives of antibiotics are disclosed. The carrier-conjugated antibiotics accumulate intracellularly, especially in phagocytic cells. Upon internalisation, the conjugates are capable of slowly hydrolysing to the original active drug molecule under physiological conditions, retaining the spectrum, efficacy and pharmacokinetic properties of the parental molecule. The composition is therefore especially effective against numerous bacterial pathogens.

The conjugate described in the "Summary" section can be prepared by methods known in the art, as well as by the synthetic routes disclosed herein. For example, one can react a transportophore having a reactive moiety with a therapeutic agent having another reactive moiety. One of the two reactive moieties is a leaving group (e.g., —Cl, OR) and the other is a derivatizable group (e.g., —OH, or —NH—). Then, the transportophore is covalently bonded to the therapeutic agent via a reaction between the two reactive moieties. In the case when a linker is present, each of the two reactive moieties, independently, is a leaving group or a derivatizable group, and each reacts with its reactive counterpart in the linker to form a covalent bond. Detailed routes including various intermediates are illustrated in the examples herein.

More specifically, a transportophore and a therapeutic agent can be directly connected or via a linking element. This element typically is a bifunctional molecule of low molecular mass, which can react subsequently with the transportophore and the therapeutic agent. Ideally the therapeutic agent can be released from this linker under physiological conditions. This may be achieved oxidatively (e.g., by action of a cytochrome C), reductively (e.g., by action of NADH), hydrolytically (e.g., by action of a protease), or initiated by radicals (e.g., by the action of superoxide radicals). The mechanisms of therapeutic agent release are not limited to the above examples.

Linkers have the formula: $F^1$-L-$F^2$
wherein:

$F^1$, $F^2$=independently a functional groups, suitable to react with a counterpart in the drug or in the carrier. $F^1$ and $F^2$ are, but are not limited to $X^1$, wherein $X^1$ is a halogen atom or a sulfonate ester or another suitable leaving group;

—C(=O)$X^2$, wherein $X^2$ is Cl, Br or I, —CHO;

—C(=O)O$R^a$ wherein $R^a$ is $(C_1$-$C_4)$alkyl or aryl, optionally substituted by 1-5 halogen atoms;

—C(=O)OC(=O)O$R^b$ wherein $R^b$ is $(C_1$-$C_5)$alkyl or $(C_1$-$C_5)$alkenyl;

—OH;

—NH$R^c$ wherein $R^c$ is H, $(C_1$-$C_4)$alkyl;

—NC$X^3$ wherein $X^3$ is S or O;

—C(=O)CR=CHR', wherein R and R' are independently —H, —$CH_3$, —Cl, —Br, —F, —O$(C_1$-$C_4)$alkyl, —C(=O)O$(C_1$-$C_4)$alkyl, —$NO_2$, —$S(=O)_k(O)_1(C_1$-$C4)$ alkyl wherein k is 0, 1 or 2 and 1 can be 0 or 1, Si$R^1R^2R^3$ wherein $R^1$,$R^2$ and $R^3$ independently are $(C_1$-$C_4)$ alkyl;

—S$X^4$ wherein $X^4$ is —H, —Cl, —$S_k(C_1$-$C_4)$alkyl, $S_k(C6$-$C_{10})$aryl wherein k is 1 or 2.

$F^1$ and $F^2$ can be connected to form a cyclic anhydride or di- or trisulfide.

L is a spacing element which is, but is not limited to,
$(C_1$-$C_8)$alkyl,
$(C_1$-$C_8)$alkenyl,
$(C_1$-$C_8)$alkynyl,
$(C_3$-$C_{10})$cycloalkyl,
$(C_6$-$C_{10})$aryl,
$(C_2$-$C_9)$heteroalkyl,
$(C_2$-$C_9)$heteroaryl.

wherein alkyl-, alkenyl, alkynyl, cycloalkyl, aryl or heteroaryl spacing elements are optionally substituted by $(C_1$-$C_6)$alkyl, 1-4 halogens, $(C_1$-$C_4)$alkoxy, $(C_1$-$C_4)$alkoxycarbonyl, hydroxy, amino, $(C_1$-$C_4)$alkylamino, $(C_1$-$C_4)$ dialkylamino, $(C_3$-$C_{10})$cycloalkyl, $(C_1$-$C_6)$ alkylcarbonyloxy, $(C_1$-$C_6)$alkylcarbonylamido, $(C_1$-$C_4)$ alkylamidocarbonyl, $(C_1$-$C_4)$dialkylamidocarbonyl, nitro, cyano, $(C_1$-$C_4)$alkylimino, mercapto and $(C_1$-$C_4)$alkylmercapto functions.

The chemicals used in the afore-mentioned methods may include, for example, solvents, reagents, catalysts, protecting group and deprotecting group reagents and the like. The methods described above may also additionally comprise steps, either before or after the steps described specifically herein, to add or remove suitable protecting groups in order to ultimately allow synthesis of the compound of the formulae described herein.

As can be appreciated by the skilled artisan, the synthetic routes herein are not intended to comprise a comprehensive list of all means by which the compounds described and claimed in this application may be synthesized. Further methods will be evident to those of ordinary skill in the art. Additionally, the various synthetic steps described above may be performed in an alternate sequence or order to give the desired compounds. Synthetic chemistry transformations and protecting group methodologies (protection and deprotection) useful in synthesizing the compounds described herein are known in the art and include, for example, those such as described in R. Larock, *Comprehensive Organic Transformations*, VCH Publishers (1989); T. W. Greene and P. G. M. Wuts, *Protective Groups in Organic Synthesis*, 2d. Ed., John Wiley and Sons (1991); L. Fieser and M. Fieser, *Fieser and Fieser's Reagents for Organic Synthesis*, John Wiley and Sons (1994); and L. Paquette, ed., *Encyclopedia of Reagents for Organic Synthesis*, John Wiley and Sons (1995) and subsequent editions thereof.

An antibiotic therapeutic activity includes any with modes of action that includes anti-bacterial agent. The antibiotics include, but are not limited to, β-lactams (including amoxicillin, ampicillin, bacampicillin, carbenicillin, cloxacillin, dicloxacillin, flucloxacillin, methicillin, mezlocillin, nafcillin, oxacillin, penicillin G, penicillin V, piperacillin, pivampicillin, pivmecillinam, ticarcillin, sulbactam, tazobactam, clavulanate), cephalosporins (cefaclor, cefadroxil, cefamandole, cefazolin, cefdinir, cefditoren, cefepime, cefixime, cefonicid, cefoperazone, cefotaxime, cefotetan, cefoxitin, cefpodoxime, cefprozil, ceftazidime, ceftibuten, ceftizoxime, ceftriaxone, cefuroxime, cephalexin, cephalothin, cephapirin, cephradine), aminoglycosides (including gentamycin, streptomycin, amikacin, kanamycin, viomycin, capreomycin), ethionamide, prothionamide, cycloserine, dapsone, clofazimine, tetracyclines (tetracycline, doxycycline, chlortetracycline, oxytetracycline, minocycline demeclocycline), oxazolidinones (linezolid, eperezolid), metronidazole, rifabutin, isoniazonid, ethambutol.

Also within the scope of this invention is a pharmaceutical composition that contains an effective amount of at least one of the conjugate of this present invention and a pharmaceutically acceptable carrier.

Pharmaceutically acceptable salts of the conjugate of this invention include those derived from pharmaceutically acceptable inorganic and organic acids and bases. Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts. Salts derived from appropriate bases include alkali metal (e.g., sodium), alkaline earth metal (e.g., magnesium), ammonium and N-(alkyl)$_4^+$ salts. This invention also envisions the quaternization of any basic nitrogen-containing groups of the compounds disclosed herein. Water or oil-soluble or dispersible products may be obtained by such quaternization.

Further, this invention covers a method of administering an effective amount of one or more conjugates of this invention to a subject (a human, a mammal, or an animal) in need of treating a disease (e.g., an infectious disease). The methods delineated herein can also include the step of identifying that the subject is in need of treatment of disorders and condition in a subject. The identification can be in the judgment of a subject or a health professional and can be subjective (e.g., opinion) or objective (e.g., measurable by a test or a diagnostic method).

The term "treating" or "treated" refers to administering a conjugate of this invention to a subject with the purpose to cure, heal, alleviate, relieve, alter, remedy, ameliorate, improve, or affect a disease, the symptoms of the disease or the predisposition toward the disease. "An effective amount" refers to an amount of a conjugate which confers a therapeutic effect on the treated subject. The therapeutic effect may be objective (i.e., measurable by some test or marker) or subjective (i.e., subject gives an indication of or feels an effect). An effective amount of the conjugate described above may range from about 0.1 mg/Kg to about 20 mg/Kg. Effective doses will also vary, as recognized by those skilled in the art, depending on route of administration, excipient usage, and the possibility of co-usage with other agents for treating a disease, including an infectious disease.

The following is a non-exclusive list of diseases and disease symptoms, which may be treated or prevented by administration of the conjugates and compositions thereof herein and by the methods herein.

Infection

Respiratory diseases of diverse origin including:

Pharyngitis ("sore throat"), Tonsilitis, Sinusitis & Otitis Media, Influenza, Laryngo-Tracheo Bronchitis (Croup), Acute Bronchiolitis, Pneumonia, Bronchopneumonia, Bronchiolitis, Bronchitis, Acute pharyngitis with fever, Pharyngoconjunctival fever, Acute follicular conjunctivitis, Pneumonia (and pneumonitis in children), COPD, asthma, Gastrointestinal diseases Gastroenteritis of diverse origin Bacterial Diseases Gram-negative bacterial infections, Enterobacteriaceae. *Escherichia coli* Infections, *E. coli* 0157:H7, Shigella dysenteriae, agent of bacillary dysentery, *Salmonella* Infections, *Salmonella typhimurium*, *Salmonella typhi*, *Klebsiella* Infections, Yaws, Brucellosis. Spirilla, *Campylobacter jejuni, Helicobacter pylori. Fusobacterium* Infections, *Burkholderia* Infections , *Pseudomonas* Infections (*Pseudomonas aeruginosa*), Whooping Cough, *Bordetella pertussis*, Gram-negative cocci: *Neisseria gonorrhoeae* and *Neisseria meningitides* agents of gonorrhea and certain types of meningitis respectively; *Neisseria* species are also implicated in acute and potentially chronic arthritis. Meningococcal Meningitis, *Haemophilus influenzae*

*Mycoplasma* Infections: *Mycoplasma pneumoniae*, Ureaplasma Urealyticum, *Mycoplasma genitalium*—, Legionellosis (Legionaires' pneumonia, Legionella pneumophilia), *Yersinia pestis* (Plague), Leptospirosis (Weil's Disease) *Leptospira*, Rat-Bite Fever (Haverhill Fever), Streptobacillus moniliformis, Tick-Borne Diseases, Spirochetes: *Borrelia burgdorferi*, (Lyme disease), Erythema migrans, Acrodermatitis Atrophicans, Borrelial Lymphocytoma), Relapsing Fever, Human Ehrlichiosis & Human Granulocytic Erlichiosis—, Tularemia, *Chlamydia* Infections, *Chlamydia pneumoniae* and Cardiovascular Disease, Ornithosis, Psittacosis (Ornithosis, Parrot Fever, *Chlamydia psittaci* Infection Among Humans, (Avian Chlamydiosis) -, *Bartonella* Infections, Q Fever, *Rickettsia* Infections, Rocky Mountain Spotted Fever, Typhus, Epidemic Louse-Borne, Scrub Typhus, Treponema pallidum, (syphilis). Vibrio Infections Gram-positive bacterial infections, Staphylococcal Infections (*Staphylococcus aureus*), Streptococcal Infections (*Streptococcus pyogenes*), Fasciitis necrotizing, Scarlet Fever, Rheumatic Fever, *Streptococcus pneumoniae*, (pneumonia, osteomyelitis, septicemia, food intoxication, toxic shock syndrome, Otitis media, meningitis, glomerulonephritis and other post-streptococcal sequelae). Anthrax, Diphtheria, Nocardia Infections , *Listeria* Infections, *Clostridium* Infections (Pseudomembranous Colitis), *Clostridium difficile, Clostridium perfringens*, Tetanus, Gas Gangrene, Botulism, Tuberculosis, Leprosy (Hansen's Disease)

Skin diseases, bacterial,

Impetigo , Actinomycosis , *Mycobacterium* Infections, Lupus vulgaris

Intracellular pathogens

*Bacillus anthracis* and *Mycobacterium tuberculosis, Mycobacterium leprae* agents of Anthrax, tuberculosis and leprosy respectively. *Rickettsias* are agents of typhus fever, Rocky Mountain Spotted Fever, Q fever. *Chlamydia* are also intracellular pathogens: *Chlamydia trachomatis* is the agent of trachoma, pelvic inflammatory disease, lymphogranuloma venereum; *Chlamydia* are also implicated in the etiology of atherosclerolis and arthritis. L. *Bartonella bacilliformis. Mycoplasmas; Mycoplasma pneumoniae,* Toxoplasmosis.

To practice the method of treating a disease, the compounds of this invention can be administered to a patient, for example, in order to treat a disease described above. The compound can, for example, be administered in a pharmaceutically acceptable carrier such as physiological saline, in combination with other drugs, and/or together with appropriate excipients. The compound described herein can, for example, be administered by injection, intravenously, intraarterially, subdermally, intraperitoneally, intramuscularly, or subcutaneously; or orally, buccally, nasally, transmucosally, topically, in an ophthalmic preparation, by inhalation, by intracranial injection or infusion techniques, with a dosage ranging from about 0.1 to about 20 mg/kg of body weight, preferably dosages between 10 mg and 1000 mg/dose, every 4 to 120 hours, or according to the requirements of the particular drug. The methods herein contemplate administration of an effective amount of compound or compound composition to achieve the desired or stated effect. Lower or higher doses than those recited above may be required. Specific dosage and treatment regimens for any particular patient will depend upon a variety of factors, including the activity of the specific compound employed, the age, body weight, general health status, sex, diet, time of administration, rate of excretion, drug combination, the severity and course of the disease, condition or symptoms, the patient's disposition to the disease, condition or symptoms, and the judgment of the treating physician.

Pharmaceutical compositions of this invention comprise a compound of this invention or a pharmaceutically acceptable salt thereof; and any pharmaceutically acceptable carrier, adjuvant or vehicle. Such compositions may optionally comprise additional therapeutic agents. The compositions delineated herein include the compounds of the formulae delineated herein, as well as additional therapeutic agents if present, in amounts effective for achieving a modulation of a disease.

The term "pharmaceutically acceptable carrier or adjuvant" refers to a carrier or adjuvant that may be administered to a patient, together with a compound of this invention, and which does not destroy the pharmacological activity thereof and is nontoxic when administered in doses sufficient to deliver a therapeutic amount of the compound.

Pharmaceutically acceptable carriers, adjuvants and vehicles that may be used in the pharmaceutical compositions of this invention include, but are not limited to, ion exchangers, alumina, aluminum stearate, lecithin, self-emulsifying drug delivery systems (SEDDS) such as d-$\alpha$-tocopherol polyethyleneglycol 1000 succinate, surfactants used in pharmaceutical dosage forms such as Tweens or other similar polymeric delivery matrices, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat. Cyclodextrins such as $\alpha$-, $\beta$-, and $\gamma$-cyclodextrin, or chemically modified derivatives such as hydroxyalkylcyclodextrins, including 2- and 3-hydroxypropyl-$\beta$-cyclodextrins, or other solubilized derivatives may also be advantageously used to enhance delivery of compounds of the formulae described herein. Oil solutions or suspensions may also contain a long-chain alcohol diluent or dispersant, or carboxymethyl cellulose or similar dispersing agents which are commonly used in the formulation of pharmaceutically acceptable dosage forms such as emulsions and or suspensions.

The pharmaceutical compositions of this invention may be orally administered in any orally acceptable dosage form including, but not limited to, capsules, tablets, emulsions and aqueous suspensions, dispersions and solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions and/or emulsions are administered orally, the active ingredient may be suspended or dissolved in an oily phase is combined with emulsifying and/or suspending agents. If desired, certain sweetening and/or flavoring and/or coloring agents may be added.

The pharmaceutical compositions of this invention may also be administered in the form of suppositories for rectal administration. These compositions can be prepared by mixing a compound of this invention with a suitable non-irritating excipient which is solid at room temperature but liquid at the rectal temperature and therefore will melt in the rectum to release the active components. Such materials include, but are not limited to, cocoa butter, beeswax and polyethylene glycols.

Topical administration of the pharmaceutical compositions of this invention is especially useful when the desired treatment involves areas or organs readily accessible by topical application. For application topically to the skin, the pharmaceutical composition should be formulated with a suitable ointment containing the active components suspended or dissolved in a carrier. Carriers for topical administration of the compounds of this invention include, but are not limited to, mineral oil, liquid petroleum, white petroleum, propylene glycol, polyoxyethylene polyoxypropylene compound, emulsifying wax and water. Alternatively, the pharmaceutical composition can be formulated with a suitable lotion or cream containing the active compound suspended or dissolved in a carrier with suitable emulsifying agents. Suitable carriers include, but are not limited to, mineral oil, sorbitan monostearate, polysorbate 60, cetyl esters wax, cetearyl alcohol, 2-octyldodecanol, benzyl alcohol and water. The pharmaceutical compositions of this invention may also be topically applied to the lower intestinal tract by rectal suppository formulation or in a suitable enema formulation. Topically-transdermal patches are also included in this invention.

The pharmaceutical compositions of this invention may be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other solubilizing or dispersing agents known in the art.

A suitable in vitro assay can be used to preliminarily evaluate a compound of this invention in treating a disease. In vivo screening can also be performed by following procedures well known in the art. For example, a macrophage phagocytosis assay can be performed as follows:

Macrophage Phagocytosis Assay

To determine the enhanced efficacy of bacterial cell killing by macrophage upon addition of compound, the RAW264.7 cells (from ATCC) were seeded at a density of ~$2.5 \times 10^5$ Macrophage/well of 24 well microtiter plates 1 day prior to assay. Assay was initiated by addition of $2.5 \times 10^6$ of freshly grown Yersinia cells (in 2×YT, 20 mM Sodium Oxalate, 20 mM $MgCl_2$). After 90 min incubation at 37° C. in 5% $CO_2$, the supernatant was aspirated and 1 ml of pre-warmed DMEM containing 100 mg/ml gentamicin to each sample. After a further 90 min. incubation, media was removed and wells were washed with 0.5 ml of pre-warmed DMEM. Medium was once again aspirated, and 200 µl of 1% Triton X-100 was added to each well, and samples were incubated for 5 min at room temperature. 800 µl of LB media was added to each well, samples were shaken briefly, and supernatants were plated at different densities to determine the output CFU.

Antibiotic Assay

The $TC_{50}$ or MIC procedure for antibiotic sensitivity testing involves an antibiotic dilution assay, which can be performed in microtitre plates. A series of twofold dilutions of each antibiotic are made in the wells, and then all wells are inoculated with a standard amount of the same test organism. After incubation, growth in the presence of the various antibiotics is observed by measuring turbidity. Antibiotic sensitivity is expressed as the concentration of the antibiotic that inhibits 50% of the growth ($TC_{50}$). Alternatively it could be expressed as the highest dilution of antibiotic that completely inhibits growth (MIC).

All references cited herein, whether in print, electronic, computer readable storage media or other form, are expressly incorporated by reference in their entirety, including but not limited to, abstracts, articles, journals, publications, texts, treatises, internet web sites, databases, patents, and patent publications.

The invention will be further described in the following example. It should be understood that these examples are for illustrative purposes only and are not to be construed as limiting this invention in any manner.

EXAMPLES

Example 1

β-Lactam Antimicrobials and Derivatives Thereof

β-lactams are by far the most widely used class of antibiotics and make up approximately 50% of the market. This class of compounds includes the penicillins, cephalosporins and carbanepems. There are numerous advantages of beta-lactams, including low-toxicity, broad-spectrum activity and good distribution within the body. β-lactam antibiotics act through inhibiting the essential penicillin binding proteins (PBPs) in bacteria, which are responsible for cell wall synthesis. β-lactam antibiotics interfere with the transpeptidase enzymes which cleave an alanine from the peptide chain through the action of a serine on the enzyme, and then finish the cross-line by making an amide bond to a lysine $NH_2$. There is a structural similarity between the terminal alanines and the penicillin. Penicillin is a substrate for the enzyme and becomes covalently bound to it.

Widespread resistance to β-lactam drugs is of growing concern in medicine. Resistance to β-lactam drugs is mediated by β-lactamases (penicillinase), which are plasmid-encoded enzymes in Gram positive bacteria that can be transferred by conjugation or transduction. A class of penicillins resistant to β-lactamases (methicillin, cloxacillin, oxacillin, dicloxacillin, and nafcillin) was developed to address this problem. Unfortunately, methicillin-resistant staphylococci (MRSA) have developed. A newer strategy to circumvent this problem is to couple β-lactam antimicrobials with inhibitors of β-lactamases (e.g. clavulanic acid, sulbactam and tazobactam). Alone these drugs are not useful therapeutic agents, but they bind βlactamases irreversibly and with high affinity preventing them from destroying the antimicrobial agent. One effective β-lactase inhibitor/β lactam antimicrobial combination is amoxicillin-clavulanic acid.

Currently available carbapenems are not absorbed from the gastrointestinal tract. Imipenem/cilastatin can be administered intravenously. A suspension form of the drug is available for intramuscular use. The more soluble meropenem can be diluted in smaller amounts of fluid and administered intramuscularly or intravenously, by bolus or short-term infusion.

In addition to resistance problems, a major disadvantage of β-lactam antibiotics is their poor intracellular availability (Renard et al. (1987) *Antimicrob. Agents Chemother.* 31: 410-416.

β-lactam/lactamase inhibitor mixtures have shown some promise against drug-resistant mycobacteria (Prabhakaran et al. (1999) *Int J Antimicrob Agents* 13: 133-5). While presence of the lactamse inhibitor at least partially overcomes problems of multidrug resistant mycobacteria, the prohibitively high doses required for effective treatment would necessitate more efficient delivery to the site of infection (i.e., inside infected cells).

I. Coupling of Penicillin G to 2' Deoxyazithromycin

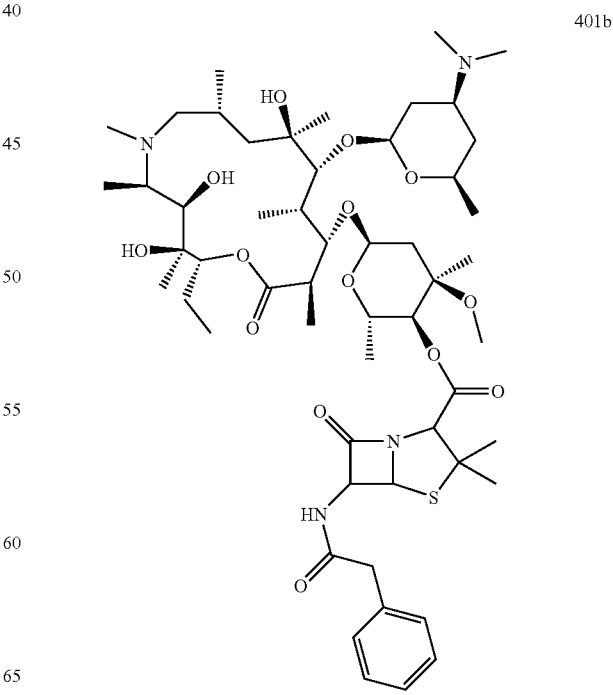

401b 5 g Azithromycin are mixed with 1.5 g p-toluol sulfonic acid chloride in 20 ml dry pyridine at 0° C. and stirred at room temperature for 72 h. The mixture is concentrated at RT in vacuo and the residue is dissolved in 30 ml dimethylsulfoxide (Hutchins et al., 1969). 750 mg of sodium borohydride are added and the mixture is heated for 8 h to 100° C. Aquous workup and subsequent chromatography yields 1.2 g of 2'-desoxyazithromycin (1-(4-Dimethylamino-3-hydroxy-6-methyl-tetrahydro-pyran-2-yloxy)-2-ethyl-3,4,10-trihydroxy-13-(5-hydroxy-4-methoxy-4,6-dimethyl-tetrahydro-pyran-2-yloxy)-3,5,6,8,10,12,14-heptamethyl-1-oxa-6-aza-cyclopentadecan-15-one).

650 mg Penicillin G (3,3-Dimethyl-7-oxo-6-phenylacetylamino-4-thia-1-aza-bicyclo[3.2.0]heptane-2-carboxylic acid) are dissolved in 8 ml dichloromethane and activated by the addition of 330 mg DCC. 1.2 g desoxyazithromycin are subjoined and the mixture is stirred at RT for 8 h. A second portion of 650 mg Penicillin G and 330 mg DCC in 8 ml dichloromethane is added and stirring is continued over night. Evaporation of the solvent and subsequent chromatography yield 450 mg of 4'[11-(4-Dimethylamino-3-hydroxy-6-methyl-tetrahydro-pyrn-2-yloxy)-2-ethyl-3,4,10-trihydroxy-13-(5-hydroxy-4-methoxy-4,6-dimethyl-tetrahydro-pyran-2-yloxy)-3,5,6,8,10,12,14-heptamethyl-1-oxa-6-aza-cyclopentadecan-15-onyl]-3,3-Dimethyl-7-oxo-6-phenylacetylamino-4-thia-1-aza-bicyclo[3.2.0]heptane-2-carboxylate (401b).

II. Coupling of Clavulanic Acid to 401b.

450 mg 4'[11-(4-Dimethylamino-3-hydroxy-6-methyl-tetrahydro-pyran-2-yloxy)-2-ethyl-3,4,10-trihydroxy-13-(5-hydroxy-4-methoxy-4,6-dimethyl-tetrahydro-pyran-2-yloxy)-3,5,6,8,10,12,14-heptamethyl-1-oxa-6-aza-cyclopentadecan-15-onyl]-3,3-Dimethyl-7-oxo-6-phenylacetylamino-4-thia-1-aza-bicyclo[3.2.0]heptane-2-carboxylate (401b) are reacted with 94 mg 3-benzyloxypropionic acid chloride at 0° C. in 5 ml of dichloromethane in the presence of 48 mg of triethylamine and a few crystals of 4-dimethylaminopyridine. After 6 h at RT the reaction is poured on ice. Aqueous workup and chromatographical purification yield 115 mg benzyloxy-propanoylated product.

115 mg of the benzyloxy-propanoylated des-2'-hydroxyazithromycin-penicillin-G-couple are hydrated with 26 mg palladium/charcoal (10% Pd) at 3 bar in ethyl acetate for 5 h. Filtration over celite, evaporation of the solvent and chromatography yield 85 mg debenzylated compound.

25 mg O-TBDMS protected clavulanic acid are activated with 15 mg DCC in 2 ml of dichloromethane. 85 mg of the product of (401d) are added and the mixture is stirred for 1 h. A second portion of activated clavulanic acid is added and the mixture is stirred for another hour. The solvent is removed and the raw mixture desilylated by treating it with 85 mg tetrabutylammoniumfluoride and 80 mg dimedone in 5 ml THF. After aqueous workup and chromatography 58 mg clavulanylated and penicillinated desoxyazithromycin (401e) are achieved.

III. Coupling of Carbenicillin to 2' Deoxyazithromycin

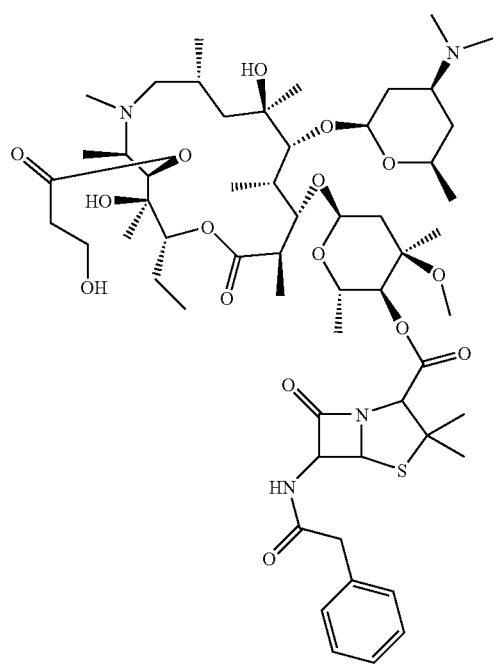

401d

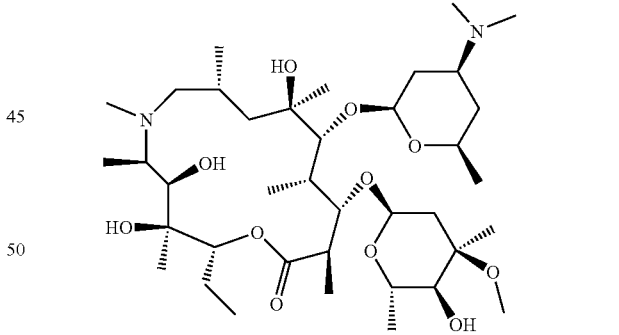

401a 575 mg Carbenicillin benzylester (6-(2-Benzyloxycarbonyl-2-phenyl-acetylamino)-3,3-dimethyl-7-oxo-4-thia-1-aza-bicyclo[3.2.0]heptane-2-carboxylic acid) are dissolved in 8 ml dichloromethane and activated by the addition of 250 mg DCC. 0.9 g desoxyazithromycin (401a) are subjoined and the mixture is stirred at RT for 8 h. A second portion of 575 mg Carbenicillin benzylester and 250 mg DCC in 8 ml dichloromethane is added and stirring is continued over night. Evaporation of the solvent and subsequent chromatography yield 203 mg of 4''-acylated product 408a.

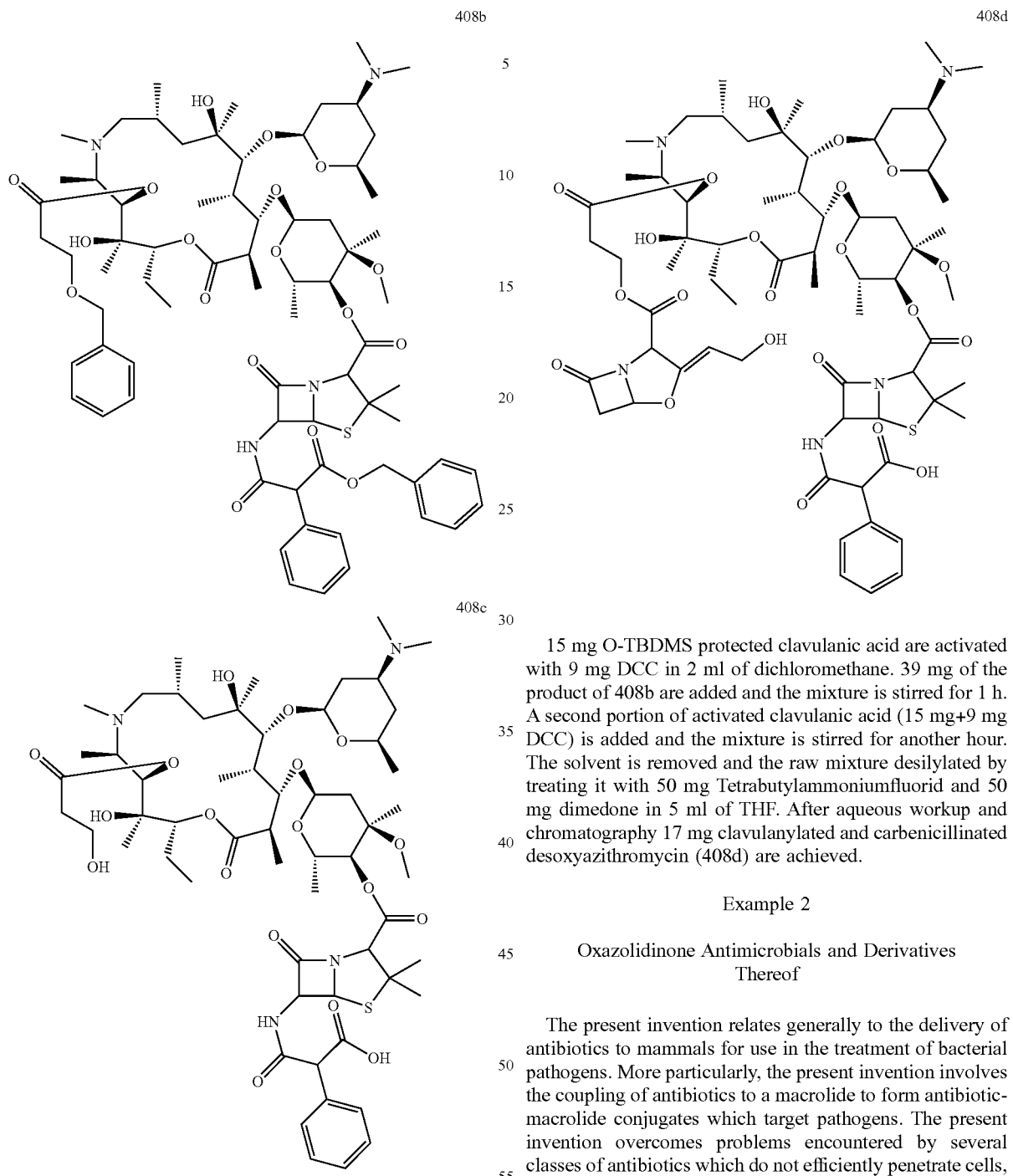

203 mg 408a are reacted with 41 mg 3-benzyloxypropionic acid chloride at 0° C. in 5 ml of dichloromethane in the presence of 21 mg of triethylamine and a few crystals of 4-dimethylaminopyridine. After 6 h at RT the reaction is poured on ice. Aqueous workup and chromatographical purification yield 62 mg benzyloxy-propanoylated product 408b. 62 mg of the benzyloxy-propanoylated des-2'-hydroxyazithromycin-penicillin-G-couple are hydrated with 20 mg palladium/charcoal (10% Pd) at 3 bar in ethyl acetate for 5 h. Filtration over celite, evaporation of the solvent and chromatography yield 39 mg debenzylated compound 408c.

15 mg O-TBDMS protected clavulanic acid are activated with 9 mg DCC in 2 ml of dichloromethane. 39 mg of the product of 408b are added and the mixture is stirred for 1 h. A second portion of activated clavulanic acid (15 mg+9 mg DCC) is added and the mixture is stirred for another hour. The solvent is removed and the raw mixture desilylated by treating it with 50 mg Tetrabutylammoniumfluorid and 50 mg dimedone in 5 ml of THF. After aqueous workup and chromatography 17 mg clavulanylated and carbenicillinated desoxyazithromycin (408d) are achieved.

Example 2

Oxazolidinone Antimicrobials and Derivatives Thereof

The present invention relates generally to the delivery of antibiotics to mammals for use in the treatment of bacterial pathogens. More particularly, the present invention involves the coupling of antibiotics to a macrolide to form antibiotic-macrolide conjugates which target pathogens. The present invention overcomes problems encountered by several classes of antibiotics which do not efficiently penetrate cells, for the treatment of, among others, intracellular pathogens.

Macrolides were selected which have been shown to have high cumulative capacity in macrophages, but which have no anti-microbial activity. The proposed oxazolidinone structures are therefore enhanced in efficacy, particularly in the treatment of intracellular pathogens.

Oxazolidinones are an appealing class of antimicrobials due to their unique bacteriostatic mechanism of action, lack of cross-resistance with other agents, good oral bioavailability, potential for structure modification, and broad spectrum of activity. Oxazolidinones with antibacterial activity are a novel class of antibiotics whose mode of action is to block protein synthesis, in particular by binding to the 50s ribosomal subunit, thereby blocking intiation of protein biosynthesis.

In in vitro susceptibility studies, linezolid was shown to have activity against a wide variety of organisms, including graph-positive cocci, gram-negative anaerobes, and mycobacteria. With few exceptions, gram-negative bacteria are resistant due to efflux. Linezolid, the first new oxazolidinone class of antibiotics, is well distributed in the body when administered orally, with virtually complete bioavailability. Good tissue penetration is achieved, with high levels in the skin structure. Metabolism yields two primary derivatives, which may accumulate in those patients with renal insufficiency. There are no major toxicity problems which emerged during clinical trials.

Partly owing to its synthetic nature and its new mechanism of action, there is an apparent lack of pre-existing resistant population. Mutational resistance has also been extremely difficult to select in staphylococci. Transferable linezolid resistance has not yet been described. Direct radiometric distribution studies, as well as efficacy studies performed using intracellular pathogens such as *Legionella* suggest that linezolid achieves modest levels of intracellular penetration (C/E ratio of ~1), thus perhaps limiting its utility in the treatment of intracellular pathogens.

I. Coupling of 1,7-Diaza-15-Crown-5 With Oxazolidinones:

rated in vacuo to dryness, 10 ml of 0.1M HCl are added and all volatile compounds are again evaporated. The residue is recrystallized from ethanol to yield 2.1 g dihydrochloride (410a).

1 g of 410a are dissolved in 15 ml dry ethanol, and 550 mg triethylamine are added. 350 mg of methyl acrylate are added. After stirring for 12 h the volatile compounds are removed and the residue is purified by chromatography to yield 620 mg of ester (410b).

620 mg of 410b are hydrolyzed by heating it with 5 ml of 0.1N HCl for 30 min to 60° C. The aqueous phase is removed by evaporation under reduced pressure to yield 720 mg of the hydrochloride (410c) after drying in vacuo.

100 mg of 410c are activated in 5 ml trichloromethane by addition of 50 mg of carbonyldiimidazole. Subsequently 80 mg 3-[4-(1-Benzyl-1,2,3,6-tetrahydro-pyridin-4-yl)-3-fluoro-phenyl]-5-hydroxymethyl-oxazolidin-2-one (U.S. Pat. No. 6,271,383) are added, and the mixture is stirred for 1 h. After aqueous workup the free base is chromatographed to yield 89 mg 3-[13-(2-Dimethylamino-acetyl)-1,4,10-trioxa-7,13-diaza-cyclopentadec-7-yl]-propionic acid 3-[4-(1-benzyl-1,2,3,6-tetrahydro-pyridin-4-yl)-3-fluoro-phenyl]-2-oxo-oxazolidin-5-ylmethyl ester (410d).

II. Coupling of 2' Deoxyazithromycin to Oxazolidinones

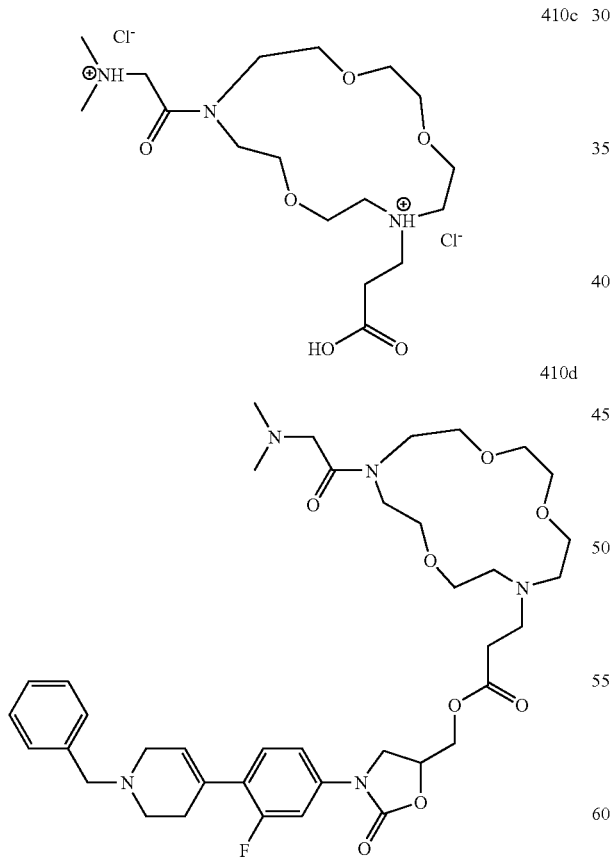

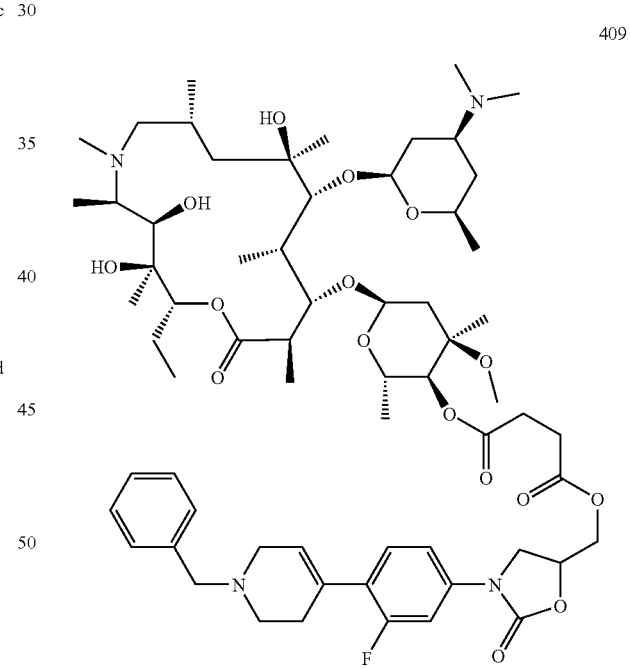

2 g of 1,7-Diaza-15-crown-5 are treated with 1.15 g of dimethylamino acetylchloride in 20 ml of dichloromethane at 0° C. The mixture is stirred for 30 min at RT and 5 ml of dry methanol are added. After 5 min the mixture is evapo- 2 g of 2' deoxyazithromycin (401a) bis-(trifluoroacetate) are reacted with 220 mg of succinic anhydride in trichloromethane under reflux for 5 h. The mixture is cooled to RT and 1.2 g of 3-[4-(1-Benzyl-1,2,3,6-tetrahydro-pyridin-4-yl)-3-fluoro-phenyl]-5-hydroxymethyl-oxazolidin-2-one trifluoroacetate (U.S. Pat. No. 6,271,383) and 520 mg DCC are added. The mixture is stirred for 1 h at RT and filtered. After evaporation of the solvent and recrystallization with 2-propanol/ethyl acetate 1.2 g of the coupled product (409) are obtained.

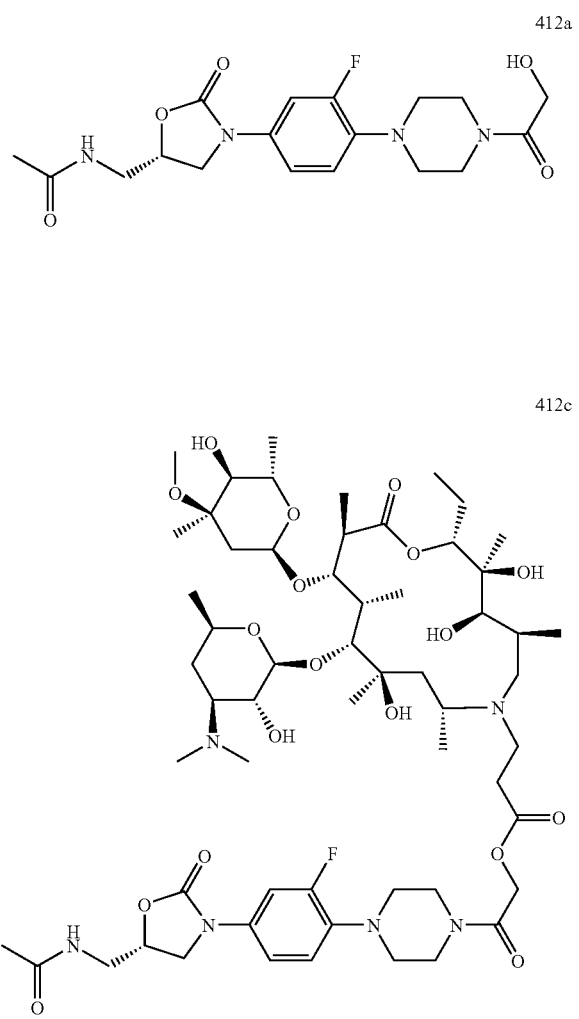

1 g of eperezolide (412a) (U-100592, Ford et al., 1996) are dissolved in 15 ml of dry dichloromethane, and 250 mg of triethylamine are added. 230 mg of acroylchloride are added. After stirring for 12 h the volatile compounds are removed by evaporation and the residue is dissolved in 20 ml of dry ethanol. 1.9 g iso-desmethyl-azithromycin are added. After stirring for 46 h, the mixture is evaporated to dryness, filtered over a short column of silica gel and chromatographed to yield 900 mg of the michael-adduct 412c.

Example 3

Cycloserine Antimicrobials and Derivatives Thereof

The resurgence of tuberculosis has been characterized by the emergence of significant numbers of drug-resistant strains. Furthermore, microorganisms of the *Mycobacterium avium* complex, opportunistic pathogens common in AIDS patients, are inherently resistant to many traditional antimycobacterial agents. Hence, the development of novel drugs for the treatment of atypical infections by *M. avium*, *Mycobacterium intracellulare*, and multiple-drug-resistant *Mycobacterium tuberculosis* is urgently needed.

The mycobacterial cell wall is an effective barrier that contributes to drug resistance. Inhibitors of cell wall biosynthesis not only are potential antimycobacterial agents but also increase mycobacterial susceptibility to other antimicrobial agents. One inhibitor of cell wall synthesis is D-cycloserine (D-4-amino-isoxazolidone [DCS]), a cyclic structural analog of D-alanine. D-Amino acids, especially D-alanine, D-gluta-mate, and D-aminopimelate, are important components of all bacterial cell walls, including those of mycobacteria. Alanine is usually available as the L stereoisomer, and the conversion to D-alanine by the cytoplasmic enzyme D-alanine racemase is required for the initial step in the alanine branch of peptidoglycan biosynthesis. D-Alanine is converted to the dipeptide D-alanyl-D-alanine in a reaction catalyzed by D-alanyl:alanine synthetase (D-alanine ligase). In *Escherichia coli*, both D-alanine racemase and D-alanine ligase are targets of DCS. Moreover, the biosynthesis of mycolyl-arabinogalactan- peptidoglycan complex is inhibited by DCS in *M. tuberculosis*, and biochemical studies indicated that D-alanine ligase is one of the targets in mycobacteria. DCS is an effective antimycobacterial agent but is rarely prescribed and used only in combined therapies due to its adverse effects. These side effects are due to binding of DCS to neuronal N-methyl aspartate receptors and inhibition of enzymes that metabolize and synthesize the neurotransmitter g-aminobutyric acid. Nevertheless, DCS is an excellent candidate for the development of a new generation of antibiotics. Two important considerations predict that rationally designed derivatives of DCS may be more efficacious antimicrobial agents. First, DCS targets participate in essential steps of cell wall synthesis. Second, DCS resistance has not yet become an important clinical problem.

I. Coupling of 1,7-Diaza-15-Crown-5 With Cycloserine:

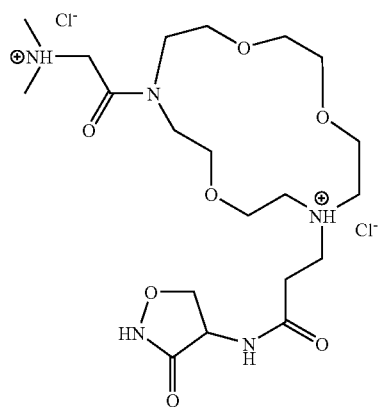

100 mg of 410c are activated in 5 ml trichloromethane by addition of 45 mg DCC. After 5 min, 21 mg cycloserine and a few crystals 4-N,N-dimethylaminopyridin are added. The mixture is stirred for 1 h, filtered, concentrated and purified by flash-chromatography to yield 72 mg of the cycloserine derivative (411).

Example 4

Metronidazole Compounds and Derivatives Thereof.

I. Coupling of Metronidazole to 2' Deoxyazithromycin

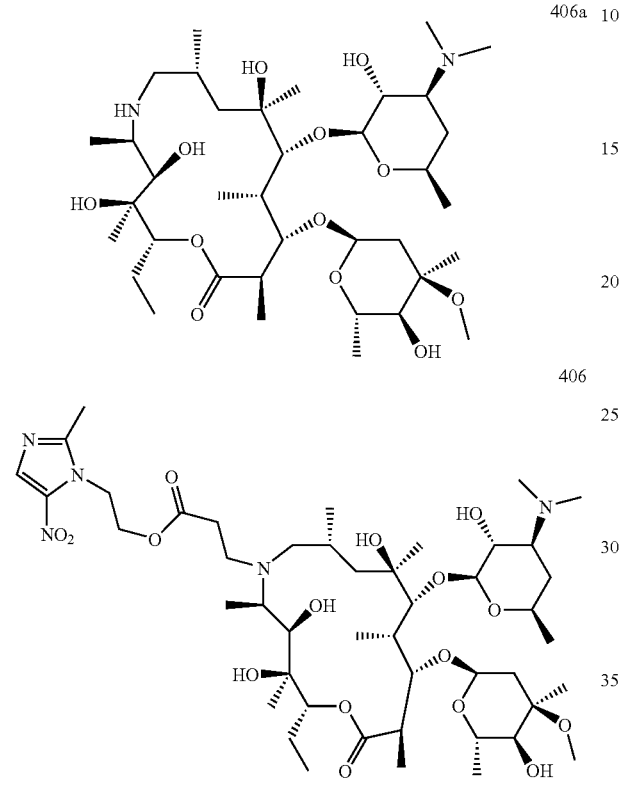

5 g Acroylchlorid are dissolved in 10 ml dichloromethane and added slowly at 0° C. to a solution of 9 g Metronidazole and 5,6 g triethylamine in 50 ml dichloromethane under vigorous stirring. After completion the temperature is raised to RT and stirring is continued for 1 h. The solvent is evaporated under reduced pressure and the product purified by flash chromatography to yield 8 g metronidazole acrylate.

920 mg metronidazole acrylate and 1 g 2'-deoxyazithromycin (406a) are dissolved in 15 ml dry ethanol and stirred for 24 h. After evaporation of the solvent and chromatography 800 mg of the coupling product (406) is obtained.

OTHER EMBODIMENTS

All of the features disclosed in this specification may be combined in any combination. Thus, unless expressly stated otherwise, each feature disclosed is only an example of a generic series of equivalent or similar features.

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:
1. A conjugate of the following formula:

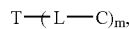

wherein
T is a transportophore,
L is a bond or a linker having a molecular weight up to 240 dalton,
C is an antibiotic therapeutic agent, and
m is 1, 2, 3, 4, 5, 6, 7, or 8,
in which the transportophore is covalently bonded to the antibiotic therapeutic agent via the bond or the linker, and the transportophore is an azithromycin derivative and the conjugate has the formula:

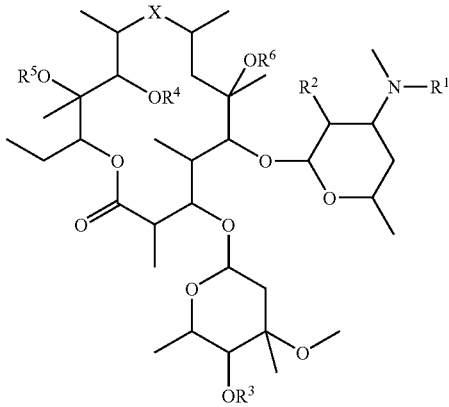

wherein
X=$N(R_7)$—$CH_2$
  $CH_2$—$N(R_7)C(=O)$
  $C(=NOR_8)$
  $C(OH)(R_9)$
  $CH(NR_{10}R_{11})$
  $C(=NR_{12})$
Y=independently a bond or a linker
Z=$C(=O)$
  $CH(R_{16})$
$R_1$=H
  $CH_3$
  $(C_2$-$C_{10})$alkyl
  $(C_1$-$C_{10})$alkenyl
  $(C_1$-$C_{10})$alkynyl
  $(C_1$-$C_8)[(C_1$-$C_4)$alkoxy]alkyl
  $(C_1$-$C_8)[(C_1$-$C_4)$alkoxy]alkenyl
  $(C_6$-$C_{10})$aryl-$(C_1$-$C_5)$alkyl
  $(C_2$-$C_9)$heteroaryl-$(C_1$-$C_5)$alkyl
  $(C_1$-$C_4)$alkyliden-$NR_{18}R_{19}$
  Y—$R_{13}$
  $C(=O)$—Y—$R_{15}$
  $C(=O)$—$R_{15}$
R2=H
  OH
  $SCH_3$;
$R_3$=H
  $C(=O)$—Y—$R_{15}$
  $C(=O)$—$R_{15}$
$R_4$=H
  $C(=O)$—Y—$R_{15}$
  $C(=O)$—$R_{15}$ $R_5$=H
or $R_4$, $R_5$ are connected by Z
$R_6$=H
  $CH_3$
$R_7$=H
  $CH_3$
  Y—$R_{13}$
  C(=O)—Y—$R_{15}$
  C(=O)—$R_{15}$
$R_8$=H
  Y—$R_{13}$
  C(=O)—$R_{17}$
$R_9$=H
  $(C_1-C_{10})$alkyl
  $(C_1-C_{10})$alkenyl
  $(C_1-C_{10})$alkynyl
  $(C_1-C_8)[(C_1-C_4)$alkoxy$]$alkyl
  $(C_1-C_8)[(C_1-C_4)$alkoxy$]$alkenyl
  $(C_6-C_{10})$aryl-$(C_1-C_5)$alkyl
  $(C_2-C_9)$heteroaryl-$(C_1-C_5)$alkyl
$R_{10}$,$R_{11}$=independently, H
  $(C_1-C_{10})$alkyl
  $(C_1-C_{10})$alkenyl
  $(C_1-C_{10})$alkynyl
  $(C_1-C_8)[(C_1-C_4)$alkoxy$]$alkyl
  $(C_1-C_8)[(C_1-C_4)$alkoxy$]$alkenyl
  $(C_6-C_{10})$aryl-$(C_1-C_5)$alkyl
  $(C_2-C_9)$heteroaryl-$(C_1-C_5)$alkyl
  $(C_1-C_4)$alkyliden-$NR_{18}R_{19}$
or $R_{10}$=H and $R_{11}$=Y—$R_{13}$
  C(=O)—Y—$R_{15}$
  C(=O)—$R_{15}$
$R_{12}$=independently, H
  $(C_1-C_{10})$alkyl
  $(C_1-C_{10})$alkenyl
  $(C_1-C_{10})$alkynyl
  $(C_1-C_8)[(C_1-C_4)$alkoxy$]$alkyl
  $(C_1-C_8)[(C_1-C_4)$alkoxy$]$alkenyl
  $(C_6-C_{10})$aryl-$(C_1-C_5)$alkyl
  $(C_2-C_9)$heteroaryl-$(C_1-C_5)$alkyl
  $(C_1-C_4)$alkyliden-$NR_{18}R_{19}$
  Y—$R_{13}$
$R_{13}$=independently, an antibiotic therapeutic agent
$R_{15}$=independently, an antibiotic therapeutic agent
$R_{16}$=independently, H
  $CH_3$
  $(C_2-C_{10})$alkyl
  $(C_1-C_{10})$alkenyl
  $(C_1-C_{10})$alkynyl
  $(C_1-C_8)[(C_1-C_4)$alkoxy$]$alkyl
  $(C_1-C_8)[(C_1-C_4)$alkoxy$]$alkenyl
  $(C_6-C_{10})$aryl-$(C_1-C_5)$alkyl
  $(C_2-C_9)$heteroaryl-$(C_1-C_5)$alkyl
  $(C_1-C_4)$alkyliden-$NR_{18}R_{19}$
  Y—$R_{13}$,
$R_{17}$=(O—$R_{20}$-aryliden)$(C_1-C_{10})$alkyl
$R_{18}$, $R_{19}$=independently, H
  $(C_1-C_{10})$alkyl
  $(C_1-C_{10})$alkenyl
  $(C_1-C_{10})$alkynyl
  $(C_1-C_8)[(C_1-C_4)$alkoxy$]$alkyl
  $(C_1-C_8)[(C_1-C_4)$alkoxy$]$alkenyl
  $(C_6-C_{10})$aryl-$(C_1-C_5)$alkyl
  $(C_2-C_9)$heteroaryl-$(C_1-C_5)$alkyl
$R_{20}$=independently, Halogen
  $(C_1-C_3)$alkyl
  $NO_2$
  CN
  $OCH_3$
  $N(CH_3)_2$.

2. The conjugate of claim 1, wherein the transportophore has a pKa value of 6.5 to 9.5.

3. The conjugate of claim 1, wherein the linker is $(C_1-C_8)$alkyl, $(C_1-C_8)$alkenyl, $(C_1-C_8)$alkynyl, $(C_3-C_{10})$cycloalkyl, $(C_6-C_{10})$aryl, $(C_2-C_9)$heteroalkyl, or $(C_2-C_9)$heteroaryl; wherein alkyl, alkenyl, alkynyl, cycloalkyl, aryl or heteroaryl is optionally substituted by $(C_1-C_6)$alkyl, 1-4 halogens, $(C_1-C_4)$alkoxy, $(C_1-C_4)$alkoxycarbonyl, hydroxy, amino, $(C_1-C_4)$alkylamino, $(C_1-C_4)$dialkylamino, $(C_3-C_{10})$cycloalkyl, $(C_1-C_6)$alkylcarbonyloxy, $(C_1-C_6)$alkylcarbonylamido, $(C_1-C_4)$alkylamidocarbonyl, $(C_1-C_4)$dialkylamidocarbonyl, nitro, cyano, $(C_1-C_4)$alkylimino, mercapto, or $(C_1-C_4)$alkylmercapto.

4. The conjugate of claim 1, wherein the antibiotic therapeutic agent is an anti-infectious agent.

5. The conjugate of claim 4, wherein the anti-infectious agent is an anti-bacterial agent.

6. A pharmaceutical composition comprising a conjugate of claim 1 and a pharmaceutically acceptable carrier.

7. A method of treating an infectious disease, comprising administering to a subject in need thereof an effective amount of a conjugate of claim 1, wherein the antibiotic therapeutic agent is an anti-infectious agent.

8. The method of claim 7, wherein the infectious disease is a bacterial disease.

9. A method for delivering an antibiotic therapeutic agent, comprising delivering a conjugate of claim 1 to a cell, wherein the conjugate includes a transportophore and an antibiotic therapeutic agent, and in the cell, the transportophore is not covalently bonded to the therapeutic agent.

10. The method of claim 9, wherein the cell is a phagocytic cell.

* * * * *